US011006738B2

(12) United States Patent
Harrington et al.

(10) Patent No.: US 11,006,738 B2
(45) Date of Patent: May 18, 2021

(54) CLEANING DEVICES HAVING SELECTIVELY FLEXIBLE OR RIGID HANDLES

(71) Applicant: Unger Marketing International, LLC, Bridgeport, CT (US)

(72) Inventors: William Harrington, Charlestown, RI (US); Susanna Stone, Bridgeport, CT (US); Kenneth John Paolini, Northford, CT (US)

(73) Assignee: UNGER MARKETING INTERNATIONAL, LLC, Bridgeport, CT (US)

( * ) Notice: Subject to any disclaimer, the term of this patent is extended or adjusted under 35 U.S.C. 154(b) by 141 days.

(21) Appl. No.: 15/879,373

(22) Filed: Jan. 24, 2018

(65) Prior Publication Data

US 2018/0206693 A1 Jul. 26, 2018

Related U.S. Application Data

(60) Provisional application No. 62/451,044, filed on Jan. 26, 2017.

(51) Int. Cl.
*A61B 5/00* (2006.01)
*A47L 13/42* (2006.01)
(Continued)

(52) U.S. Cl.
CPC ............ *A46B 5/0037* (2013.01); *A46B 5/005* (2013.01); *A46B 5/007* (2013.01); *A46B 5/0016* (2013.01);
(Continued)

(58) Field of Classification Search
CPC ..... A46B 5/002; A46B 5/0033; A46B 5/0037; A46B 5/0054; A46B 5/0062;
(Continued)

(56) References Cited

U.S. PATENT DOCUMENTS 1,360,615 A * 11/1920 Bolard .................. A46B 17/06 15/106
1,694,636 A 12/1928 Barker
(Continued)

FOREIGN PATENT DOCUMENTS

CA 2519035 * 10/2006
DE 1986144 5/1968
(Continued)

OTHER PUBLICATIONS

European Search Report for Application No. 18153646.7-101813366184 dated Aug. 1, 2018; 7 pgs.
(Continued)

*Primary Examiner* — Mark Spisich
(74) *Attorney, Agent, or Firm* — Cantor Colburn LLP

(57) ABSTRACT

A cleaning device is provided that includes a handle, a cleaning implement, a flexible neck, and a collar. The cleaning implement depends from one end the handle. The flexible neck is positioned to allow flexion of the handle. The collar moves with respect to the flexible neck between a first position where movement of the flexible neck is unrestricted by the collar and a second position where movement of the flexible neck is restricted by the collar.

14 Claims, 15 Drawing Sheets

(51) Int. Cl.

| | |
|---|---|
| ***B25G 1/04*** | (2006.01) |
| ***B25G 1/02*** | (2006.01) |
| ***B25G 3/38*** | (2006.01) |
| ***A46B 5/00*** | (2006.01) |
| ***A47L 13/38*** | (2006.01) |
| ***A47L 13/46*** | (2006.01) |
| ***A47L 13/16*** | (2006.01) |
| ***A47L 13/256*** | (2006.01) |
| ***A47L 13/257*** | (2006.01) |

(52) U.S. Cl.

CPC .......... *A46B 5/0062* (2013.01); *A46B 5/0066* (2013.01); *A46B 5/0079* (2013.01); *A47L 13/16* (2013.01); *A47L 13/256* (2013.01); *A47L 13/257* (2013.01); *A47L 13/38* (2013.01); *A47L 13/42* (2013.01); *A47L 13/46* (2013.01); *B25G 1/02* (2013.01); *B25G 1/04* (2013.01); *B25G 3/38* (2013.01); *Y10S 16/90* (2013.01); *Y10T 403/451* (2015.01); *Y10T 403/54* (2015.01)

(58) Field of Classification Search

CPC ..... A46B 5/0066; A46B 5/007; A46B 5/0075; A46B 5/0079; A46B 5/0091; A46B 7/02; A46B 7/06; A46B 5/005; A46B 5/0016; B25G 1/01; B25G 1/02; B25G 3/38; Y10T 403/451–453; Y10T 403/54; Y10S 16/90

USPC .. 15/144.1, 144.2, 172, 244.2, 144.3, 144.4, 15/106, 115; 16/900; 403/291, 220–229

See application file for complete search history.

(56) References Cited

U.S. PATENT DOCUMENTS

| | | | | | |
|---|---|---|---|---|---|
| 1,977,180 | A * | 10/1934 | Forbes | A47L 13/24 | 403/100 |
| 1,982,910 | A * | 12/1934 | Forbes | A47L 13/24 | 403/100 |
| 2,998,614 | A | 9/1961 | Winch | | |
| 3,058,139 | A | 10/1962 | Dryden | | |
| 3,332,103 | A | 7/1967 | Case | | |
| 3,407,424 | A * | 10/1968 | Lanzarone | A47L 13/24 | 15/145 |
| 4,328,604 | A | 5/1982 | Adams | | |
| 4,520,526 | A | 6/1985 | Peters | | |
| D296,271 | S | 6/1988 | Kobayashi | | |
| 4,794,663 | A * | 1/1989 | Vosbikian | A47L 13/24 | 15/144.1 |
| 4,829,621 | A | 5/1989 | Phenegar | | |
| 5,158,532 | A | 10/1992 | Peng | | |
| 5,315,732 | A | 5/1994 | Huefner | | |
| 5,333,345 | A * | 8/1994 | O'Donnell | A46B 5/0062 | 15/144.1 |
| 5,400,457 | A * | 3/1995 | Ridgley | A46B 5/0033 | 15/144.4 |
| 5,491,863 | A | 2/1996 | Dunn | | |
| 5,598,596 | A | 2/1997 | Jones et al. | | |
| 5,630,244 | A * | 5/1997 | Chang | A46B 5/0062 | 15/143.1 |
| 5,709,003 | A | 1/1998 | Batch | | |
| 5,878,459 | A | 3/1999 | McParland | | |
| 5,967,152 | A | 10/1999 | Rimkus | | |
| 6,015,293 | A | 1/2000 | Rimkus | | |
| 6,132,126 | A | 10/2000 | Sheffler | | |
| 6,134,738 | A | 10/2000 | Weber | | |
| 6,154,913 | A | 12/2000 | Burton | | |
| 6,192,525 | B1 | 2/2001 | Tash | | |
| 6,237,182 | B1 | 5/2001 | Cassar | | |
| 6,279,189 | B1 * | 8/2001 | Cassar | A46B 5/0062 | 15/144.1 |
| 6,530,707 | B1 | 3/2003 | Byrne | | |
| 6,546,588 | B1 | 4/2003 | Black | | |
| 6,948,209 | B2 | 9/2005 | Chan | | |
| 6,990,706 | B2 * | 1/2006 | Broecker | A46B 5/0062 | 15/143.1 |
| 7,017,222 | B2 | 3/2006 | Dunn | | |
| 7,213,292 | B1 | 5/2007 | Tucker | | |
| 7,334,286 | B2 | 2/2008 | Kayser | | |
| 7,344,327 | B2 | 3/2008 | Gueret | | |
| 7,356,869 | B2 | 4/2008 | Knopow | | |
| D579,615 | S | 10/2008 | Ames | | |
| 7,640,617 | B2 * | 1/2010 | Kennedy | A47L 13/20 | 15/144.1 |
| 7,716,777 | B2 | 5/2010 | Lee | | |
| 7,745,354 | B2 | 6/2010 | Tsuchiya | | |
| 7,784,141 | B2 | 8/2010 | Knopow | | |
| 8,046,865 | B2 | 11/2011 | Knopow | | |
| 8,123,712 | B2 | 2/2012 | Julius | | |
| 8,136,196 | B2 | 3/2012 | Dingert | | |
| D663,530 | S | 7/2012 | Duwa | | |
| D683,544 | S | 6/2013 | Duwa | | |
| 8,984,701 | B2 * | 3/2015 | Tussy | A46B 5/0058 | 15/143.1 |
| 9,066,583 | B2 | 6/2015 | Kayser | | |
| 9,167,882 | B2 | 10/2015 | Stefanson | | |
| 9,339,104 | B2 | 5/2016 | O'Neill | | |
| 2001/0047556 | A1 | 12/2001 | Weihrauch | | |
| 2002/0148061 | A1 | 10/2002 | Tanaka | | |
| 2004/0011382 | A1 | 1/2004 | Kingry | | |
| 2004/0143923 | A1 | 7/2004 | Bensussan | | |
| 2004/0177863 | A1 | 9/2004 | McKay | | |
| 2005/0144749 | A1 | 7/2005 | Yamada | | |
| 2006/0070198 | A1 | 4/2006 | DeRoma | | |
| 2006/0234899 | A1 | 10/2006 | Nekmard et al. | | |
| 2007/0020020 | A1 | 1/2007 | Bobrosky et al. | | |
| 2007/0028409 | A1 | 2/2007 | Yamada | | |
| 2008/0028555 | A1 | 2/2008 | Petner | | |
| 2008/0028560 | A1 | 2/2008 | Policicchio | | |
| 2008/0032577 | A1 | 2/2008 | Policicchio | | |
| 2010/0115722 | A1 | 5/2010 | Malloy | | |
| 2011/0107551 | A1 * | 5/2011 | Cassar | A46B 5/0062 | 15/363 |
| 2011/0226638 | A1 | 9/2011 | Hoadley | | |
| 2012/0183344 | A1 | 7/2012 | Habinger | | |
| 2013/0298342 | A1 * | 11/2013 | Cassar | A46B 5/0066 | 15/144.1 |
| 2014/0099154 | A1 | 4/2014 | O'Neill | | |
| 2014/0137352 | A1 | 5/2014 | Golla | | |
| 2016/0029859 | A1 | 2/2016 | Harrington | | |
| 2016/0249733 | A1 * | 9/2016 | Tebbe | A46B 5/0037 | 15/143.1 |

FOREIGN PATENT DOCUMENTS

| | | | |
|---|---|---|---|
| DE | 1995617 | | 10/1968 |
| DE | 4435888 | | 4/1996 |
| DE | 202013005066 | | 8/2013 |
| FR | 2371178 | * | 6/1978 |
| GB | 418871 | A | 11/1934 |
| GB | 651508 | A | 4/1951 |
| JP | 2-257904 | * | 10/1990 |
| WO | 2013063568 | | 5/2013 |
| WO | 2013063568 | A1 | 5/2013 |

OTHER PUBLICATIONS

European Search Report for Application No. 18153649.1-1018 dated Jun. 8, 2018; 8 pgs.

European Office Action; International Application No. 18153646.7-1016; International Filing Date: Jan. 26, 2018; dated Aug. 20, 2020; 5 pages.

European Office Action; International Application No. 18153649.1-1016; International Filing Date: Jan. 26, 2018; dated Aug. 21, 2020; 6 pages.

(56) References Cited

OTHER PUBLICATIONS

U.S. Non-Final Office Action; U.S. Appl. No. 15/879,378, filed Jan. 24, 2018; dated Oct. 29, 2020; 9 pages.

* cited by examiner

CLEANING DEVICES HAVING SELECTIVELY FLEXIBLE OR RIGID HANDLES

CROSS REFERENCE TO RELATED APPLICATIONS

This application claims the benefit of U.S. Provisional application Ser. No. 62/451,044 filed on Jan. 26, 2017, the entire contents of which are incorporated by reference. This application also incorporates by reference the entire contents of U.S. application Ser. No. 14/791,531 filed Jul. 5, 2015, now U.S. Pat. No. 10,258,205.

BACKGROUND

1. Field of the Invention

The present disclosure is related to cleaning devices. More particularly, the present disclosure is related to cleaning devices that are selectively flexible or rigid—allowing for cleaning of difficult to reach locations.

2. Description of Related Art

Cleaning devices that have handles and cleaning implements are known. These cleaning implements can include, but are not limited to, dusting devices, wiping devices, brushing devices, mopping devices, and others.

In some cleaning applications, it is desired for the cleaning device to resiliently flex or bend (hereinafter "flex") to allow cleaning in hard to reach places.

In other applications, it is desired for the cleaning device to only selectively flex, to provide a more rigid cleaning device as in Applicant's own US Publication No. 2016/0029859A1, which is incorporated herein by reference.

Accordingly, it has been determined by the present disclosure that there is a continuing need for new and improved cleaning devices having selectively flexible or rigid handles.

SUMMARY

A cleaning device is provided that includes a handle, a cleaning implement, a flexible neck, and a collar. The cleaning implement depends from one end the handle. The flexible neck is positioned to allow flexion of the handle. The collar moves with respect to the flexible neck between a first position where movement of the flexible neck is unrestricted by the collar and a second position where movement of the flexible neck is restricted by the collar.

In some embodiments either alone or together with any one or more of the aforementioned and/or after-mentioned embodiments, the collar moves with respect to the flexible neck in a manner selected from the group consisting of sliding along the longitudinal axis, rotating around the longitudinal axis, rotating about an axis perpendicular to the longitudinal axis, radial clamping onto the longitudinal axis, and any combinations thereof.

In some embodiments either alone or together with any one or more of the aforementioned and/or after-mentioned embodiments, the cleaning device further includes a telescoping device that allows the handle to telescope between extended and retracted positions.

In some embodiments either alone or together with any one or more of the aforementioned and/or after-mentioned embodiments, the flexible neck provides a first level of flexion in a first orientation, but a second, lower level of flexion in a second orientation.

In some embodiments either alone or together with any one or more of the aforementioned and/or after-mentioned embodiments, the flexible neck provides equal levels of flexion in all orientations.

In some embodiments either alone or together with any one or more of the aforementioned and/or after-mentioned embodiments, the flexible neck is a single unitary member having an upper region, a lower region, and a rib that are formed together with an elastomeric member over at least portions of the rib In some embodiments either alone or together with any one or more of the aforementioned and/or after-mentioned embodiments, the elastomeric member encases the rib.

In some embodiments either alone or together with any one or more of the aforementioned and/or after-mentioned embodiments, the elastomeric member is over molded onto the rib.

In some embodiments either alone or together with any one or more of the aforementioned and/or after-mentioned embodiments, the elastomeric member provides elastomeric or resilient properties to the flexible neck.

In some embodiments either alone or together with any one or more of the aforementioned and/or after-mentioned embodiments, the elastomeric member has different elastomeric properties on one side of the rib as compared to an opposite side of the rib.

In some embodiments either alone or together with any one or more of the aforementioned and/or after-mentioned embodiments, the cleaning device further includes features that secure the collar in a position selected from the group consisting of the first position, the second position, a plurality of positions between the first and second position, and any combinations thereof.

In some embodiments either alone or together with any one or more of the aforementioned and/or after-mentioned embodiments, the features are positioned on the flexible neck, the collar, or both the flexible neck and the collar.

In some embodiments either alone or together with any one or more of the aforementioned and/or after-mentioned embodiments, the cleaning device further includes a nested detail cleaning device disposed within a free end of the handle opposite cleaning implement.

In some embodiments either alone or together with any one or more of the aforementioned and/or after-mentioned embodiments, the neck has a stiffness ratio of flexion when the collar is in the first position to when the collar is in the second position of at least 1:2.

A cleaning device is provided that includes a handle, a cleaning implement depending from one end the handle, and a detail cleaning device nested within a free end of the handle opposite the cleaning implement.

In some embodiments either alone or together with any one or more of the aforementioned and/or after-mentioned embodiments, the handle includes a first opening and the nested detail cleaning device comprises a second opening. The first and second openings, in an assembled position, are in registration with one another and allow a user to apply a force onto the nested detail cleaning device to force the nested device into or out of the handle.

In some embodiments either alone or together with any one or more of the aforementioned and/or after-mentioned embodiments, the handle includes a pair of elongated openings at the free end and the nested detail cleaning device include a corresponding pair of protrusions. The pair of elongated openings, in an assembled position, receive the pair of protrusions therein and allow a user to apply a force to the pair of protrusions to insert or remove the nested detail cleaning device from the handle in a longitudinal direction of the handle.

In some embodiments either alone or together with any one or more of the aforementioned and/or after-mentioned embodiments, the pair of elongated openings having at least one opening of with a locking feature. The at least one protrusion of the pair of protrusions acts on, during insertion and removal, the locking feature to deflect one or more regions of handle that are proximate to the pair of elongated openings outward so that the pair of protrusions can pass over the locking feature.

In some embodiments either alone or together with any one or more of the aforementioned and/or after-mentioned embodiments, the cleaning device further includes a flexible neck positioned to allow flexion of the handle.

In some embodiments either alone or together with any one or more of the aforementioned and/or after-mentioned embodiments, the cleaning device further includes a collar that moves with respect to the flexible neck between a first position where movement of the flexible neck is unrestricted by the collar and a second position where movement of the flexible neck is restricted by the collar.

In some embodiments either alone or together with any one or more of the aforementioned and/or after-mentioned embodiments, the flexible neck provides a first level of flexion in a first orientation, but a second, lower level of flexion in a second orientation or provides equal levels of flexion in all orientations.

The above-described and other features and advantages of the present disclosure will be appreciated and understood by those skilled in the art from the following detailed description, drawings, and appended claims.

DETAILED DESCRIPTION

Figure 1:
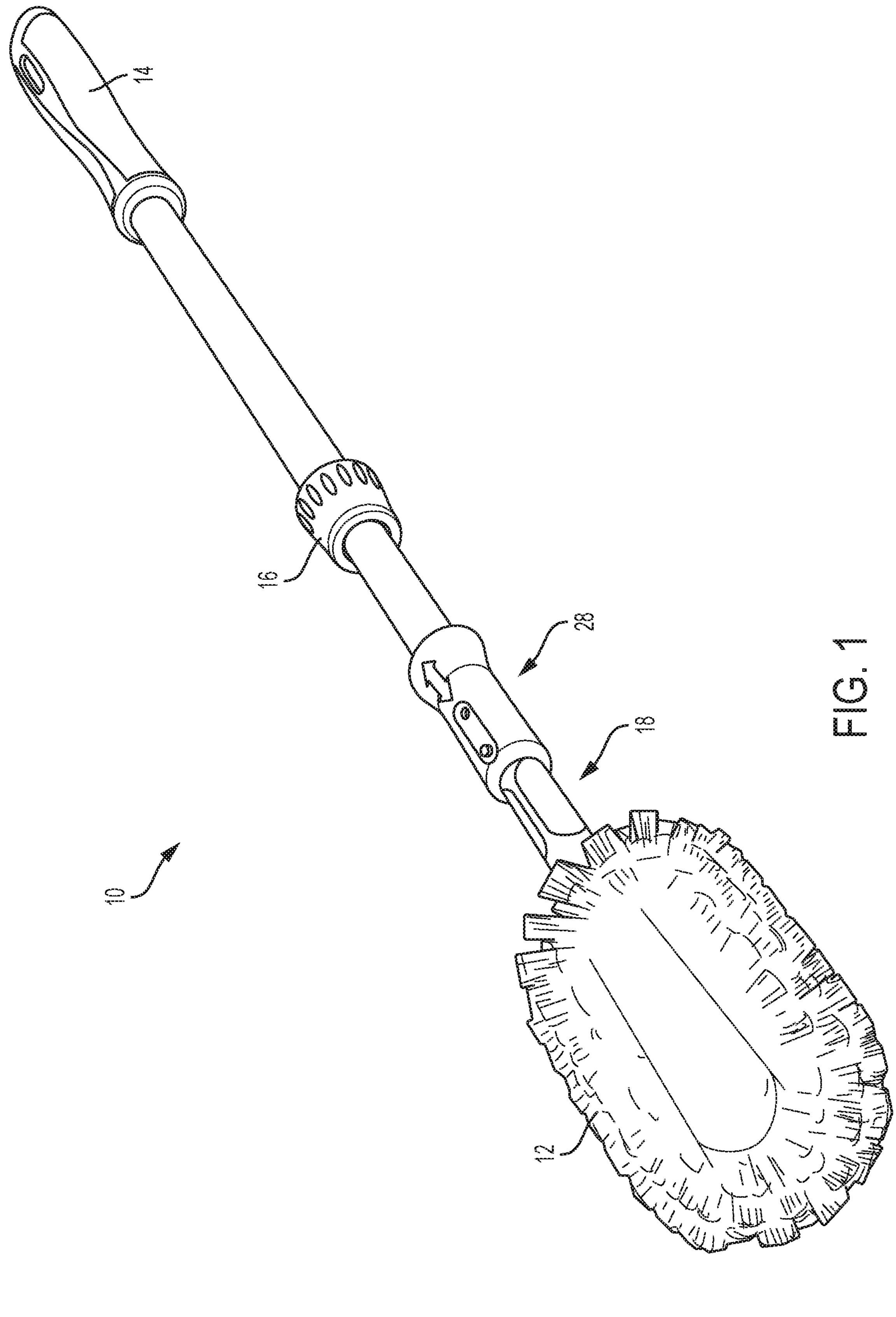
FIG. 1 is perspective view of a cleaning device according to the present disclosure.

Referring now to the drawings and in particular to FIGS. 1 through 4C, a cleaning device 10 according to the present disclosure is shown, which is configured to allow for cleaning of hard to reach locations and has a selectively flexible or rigid handle.

Cleaning device 10 is shown by way of example as having a cleaning implement 12 illustrated as a brush, but of course it is contemplated by the present disclosure for device 10 to find use with other cleaning implements such as, but not limited to, a duster, a scrubber, a scraper, a squeegee, an applicator, mop, and any combinations thereof. Device 10 can include one or more features such as, but not limited to, a handle or pole 14 (hereinafter "handle") and a telescoping device 16, which allows the handle to be telescope between extended and retracted positions in a known manner.

Figure 2A:
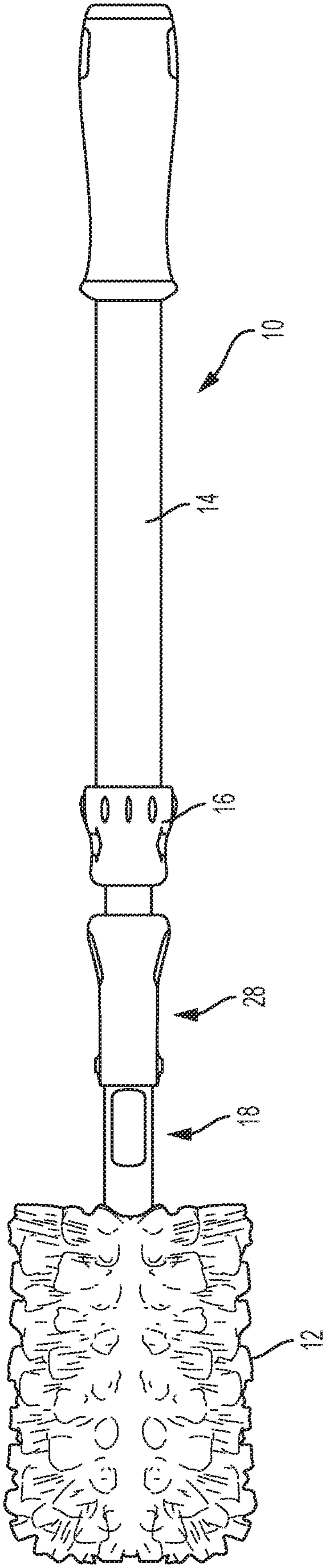
FIGS. 2A and 2B are top and side views of the cleaning device of FIG. 1.
Figure 2B:
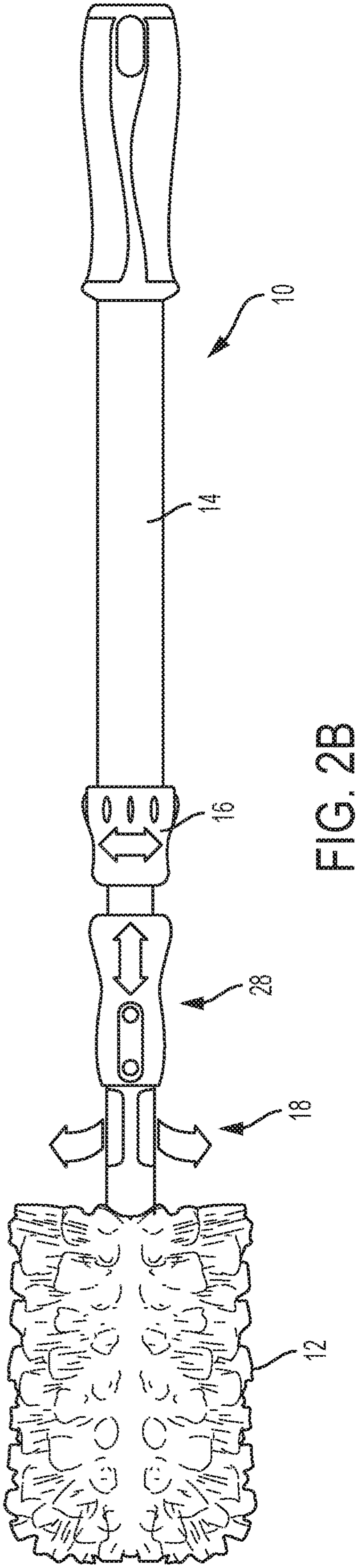

Advantageously, device 10 includes a flexible neck 18. For example, neck 18 can be as disclosed in Applicant's U.S. application Ser. No. 14/791,531, which is incorporated by reference herein—where the neck provides a first level of flexion in a first orientation as shown in FIG. 2A, but a second, lower level of flexion in a second orientation shown in FIG. 2B.

As used herein, the term "orientation" shall mean a degree of rotation about a longitudinal axis of handle 14. In this manner, the user can use device 10 in the first orientation to allow the cleaning device to flex into hard to reach places and can use the same device in the second orientation to apply a higher level of cleaning force.

Figures 3A, 3B, 3C:
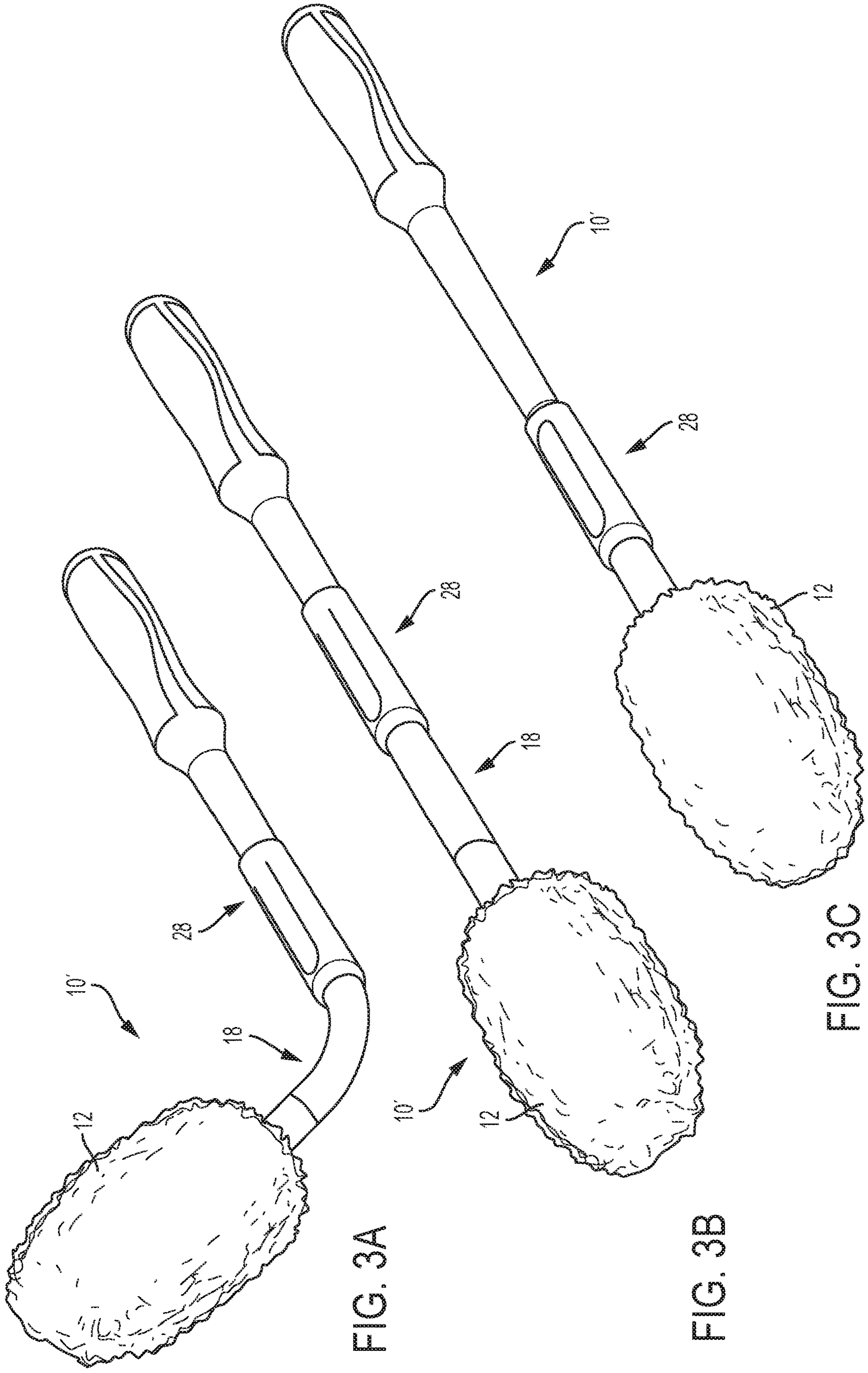
FIGS. 3A, 3B, and 3C schematically depict an alternate embodiment of a cleaning device according to the present disclosure in various use positions.

However, it is also contemplated by the present disclosure for the neck to provide equal levels of flexion in all orientations as shown in device 10' of FIGS. 3A-3C. Here, device 10' includes neck 18 that is particularly configured to be rotated while in a flexed position, allowing the neck to act as a universal joint during rotation. It should be noted that device 10' of FIGS. 3A-3C is shown without telescoping device 16. It should also be noted that device 10' is configured with neck 18 completely encased in elastomeric material as discussed in more detail below.

In this embodiment, device 10' provides the same level of flexion regardless of how the user orients cleaning implement 12 with respect to the surface being cleaned.

The terms "rigid", "inflexible", "flexible", and the like are obviously terms of degree and are used herein to describe the general properties neck 18.

Strictly speaking, neck 18 allows flexion, upon application of sufficient force, in the first orientation, but resists flexion in the second orientation. Neck 18 can have a stiffness ratio of flexion in the first orientation to flexion the second orientation of between 2:1 to 100:1, more preferably between 5:1 and 50:1, with about 10:1 being most preferred.

Figure 4A:
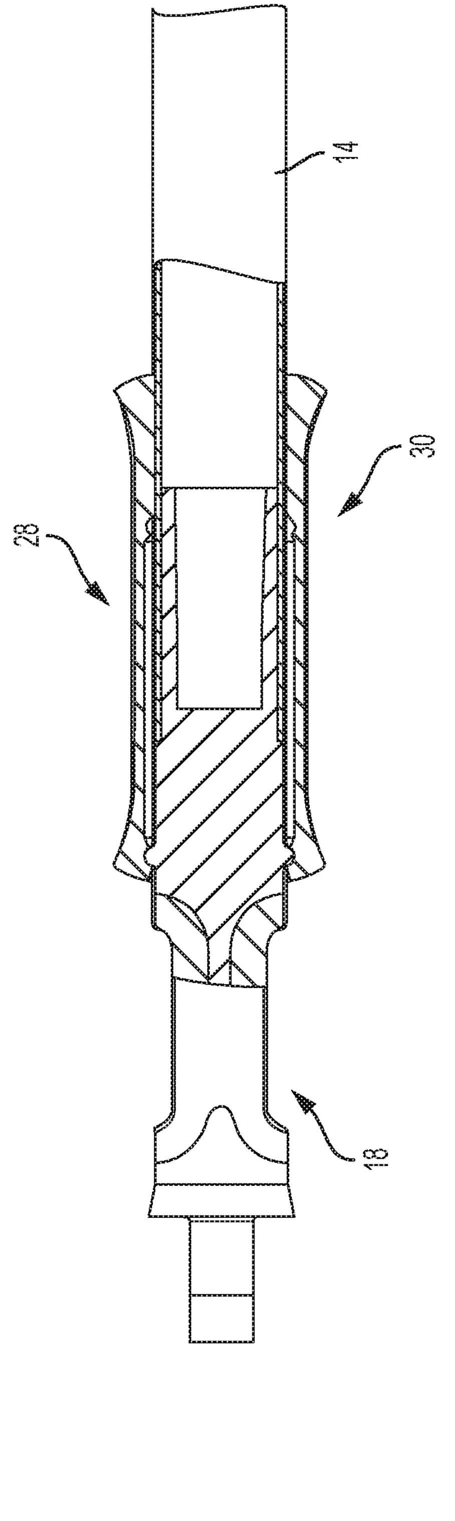
FIG. 4A illustrates a partial sectional view of the cleaning device of FIG. 1 having the flexion collar shown in a first position.
Figure 4C:
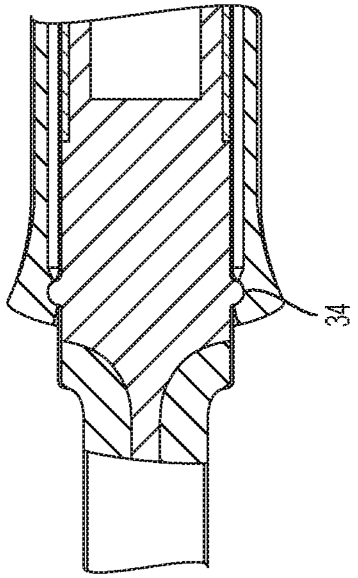
FIG. 4C illustrates a magnified portion of the cleaning device of FIG. 4B with the flexion collar shown in the second position.
Figure 4B:
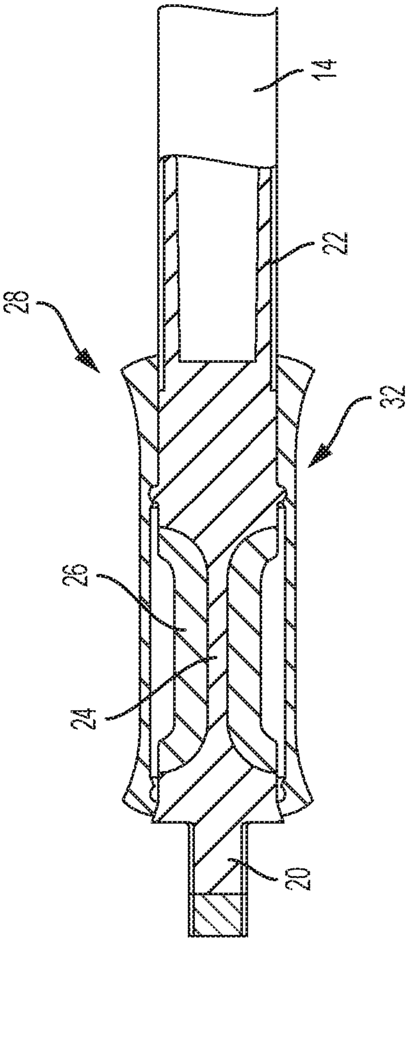
FIG. 4B illustrates the cleaning device of FIG. 4A with the flexion collar shown in a second position.

Neck 18 is, preferably, molded as a single unitary member with upper region 20, a lower region 22, and a rib 24 formed together—with an elastomeric member 26 molded over at least portions of the rib—best seen in FIG. 4B. In some embodiments, elastomeric member 26 is molded over the entire rib 24 so that the rib is encased by the elastomeric member as in FIGS. 3A-3C.

It is noted that rib 24 in the embodiment of FIGS. 1, 2A-2B, and 4A-4C has a rectangular cross section that allows for the first and second levels of flexion depending on the orientation, while rib 24 in the embodiment of FIGS. 3A-3B has a circular cross section that allows for equal levels of flexion regardless of the orientation.

Elastomeric member 26 is, preferably, over molded onto rib 24 during manufacture using a material such as, but not limited to a thermoplastic elastomer (TPE) or thermoplastic rubber (TPR). Of course, it is contemplated by the present disclosure for elastomeric member 26 to be secured to neck 18 in any desired manner such as, but not limited to, mechanical fastening, thermal fastening, adhesive fastening, and any combinations thereof.

Advantageously, elastomeric member 26 provides, at least in part, elastomeric or resilient properties to neck 18. Accordingly, the degree of flexibility of neck 18 can be calibrated or tuned by adjusting the dimensions, shape, features, and materials of elastomeric member 26. For example, the harder or higher the durometer of elastomeric member 26, the less flexible neck 18 will be in the first orientation. Conversely, the softer or lower the durometer of elastomeric member 26, the less rigid neck 18 will be will be in the first orientation. In a preferred embodiment, elastomeric member 26 has a Shore A durometer of between about 40 and 90, with about 60 being preferred. Again, it should be recognized that one or more of the attributes of elastomeric member 26 can be varied along the length to provide the desired flexion.

Moreover, it is contemplated for elastomeric member 26 to have different elastomeric properties (i.e., material or other attributes like thickness, shape, etc.) on one side of rib 24 than on the other side of the rib. In this manner, cleaning device 10 can be configured to have one level of flexibility when bending in one direction and a different level of flexibility when bending in the opposite direction. Moreover, it is contemplated that this embodiment of elastomeric member 26 can be combined with rib 24 of rectangular or circular cross sections.

In use, cleaning member 10 can be oriented to allow the user deflect or flex neck 18 so that cleaning implement 12 can be presented to hard to reach places as needed.

Importantly, device 10 has a flexion collar 28 that moves with respect to neck 18 between a first position 30 where movement of the neck is unrestricted by the collar as shown in FIGS. 2A, 2B, 3A, 3B, and 4A) and a second position 32 where movement of the neck is restricted by the collar (FIGS. 3C, 4B, and 4C).

Neck 18—when the neck provides equal levels of flexion in all orientations—can have a stiffness ratio of flexion when collar 28 is in first position 30 to when collar 28 is in second position 32 of at least 1:2, more preferably at least 1:5, most preferably at least 1:20.

In other embodiments where neck 18 provides different levels of flexion in different orientations, the neck can have a stiffness ratio of flexion—in the second or stiffer orientation—when collar 28 is in first position 30 to when collar 28 is in second position 32 of at 1:2, more preferably 1:5, most preferably 1:20.

In some embodiments, neck 18 can have a flexion—when collar 28 is in first position 30—of about 1 N/m in the first orientation and a flexion of 5 N/m in the second orientation, but can have a flexion—when collar 28 is in second position 32—of 10 N/m regardless of the orientation.

In the illustrated embodiment, the movement of neck 18 is shown as a linear or sliding movement along the longitudinal axis of handle 14.

However, it is contemplated by the present disclosure for collar 28 to move in any desired manner between the first and second positions. For example, it is contemplated by the present disclosure for collar 28 to have a movement including sliding along the longitudinal axis, rotating around the longitudinal axis, rotating about an axis perpendicular to the longitudinal axis, radial clamping onto the longitudinal axis, and any combinations thereof.

Preferably, device 10 is configured to provide feedback to the user during movement of collar 28 to first and second positions 30, 32. The feedback can be one of an audible feedback, a tactile feedback, and combinations thereof.

In some embodiments, device 10 is configured to selectively hold collar 28 in the first position 30 or the second position 32. In this manner, collar 28 is configured to allow the user to device with two discrete levels of flexion (first position 30 or second position 32).

In other embodiments, device 10 is configured to selectively hold collar 28 in a plurality of select positions between the first position 30 and the second position 32. In this manner, collar 28 is configured to allow the user to device with variable levels of flexion.

Collar 28 can be selectively held in the desired position in any desired manner such as, but not limited to, one or more locking features 34 illustrated in FIG. 4C. Features 34 can be on neck 18, collar 28, or both the neck and the collar. Of course, it is also contemplated by the present disclosure for features 34 to be in any position on device 10, such as but not limited to on handle 14.

Figure 4D:
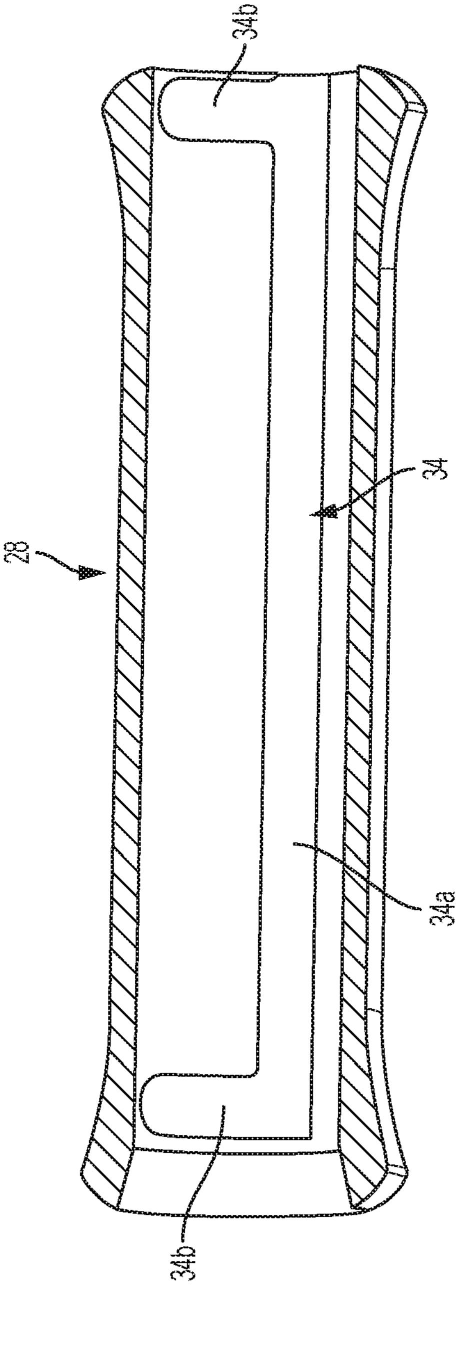
FIG. 4D illustrates a partial sectional view of another exemplary embodiment of the flexion collar.
Figure 4E:
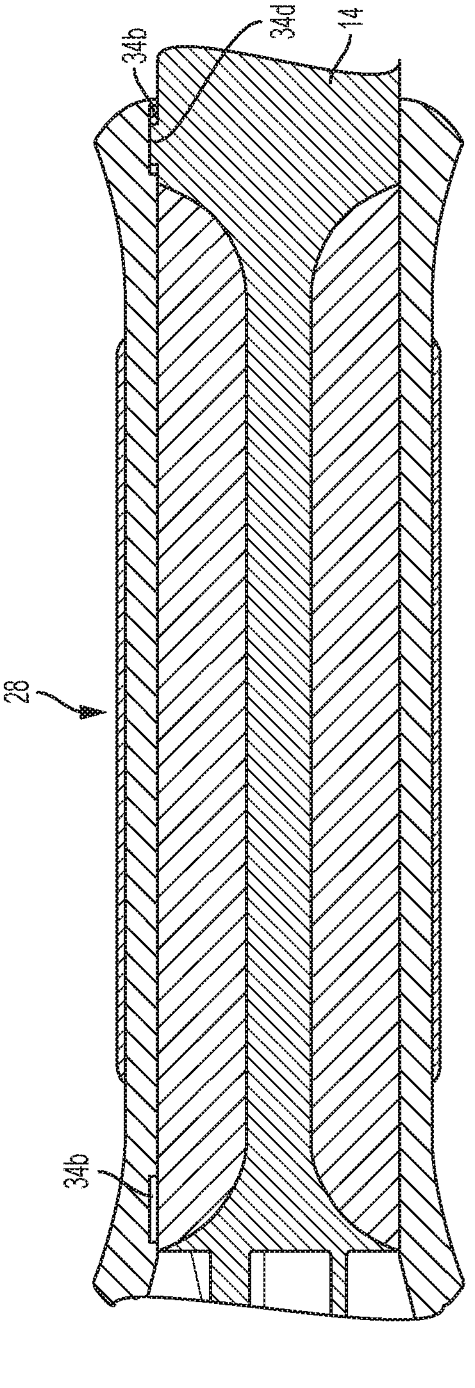
FIG. 4E illustrates a partial sectional view of the cleaning device of FIG. 1 having the flexion collar of FIG. 4D.

In one embodiment illustrated in FIGS. 4D and 4E, collar 28 is configured to move in a combination of a sliding along the longitudinal axis and rotating around the longitudinal axis. Here, collar 28 includes feature 34*a* that has both a longitudinal region 34*b* and a rotational region 34*c*, where feature 34*a* cooperates with a corresponding feature 34*d* on handle 14. Rotational region 34*c* allows collar 28 to slide along the longitudinal axis, while the rotational region 34*c* allows collar 28 to rotate about the longitudinal axis. Rotational regions 34*c* (two shown) correlate to the first and second positions 30, 32, respectively.

Accordingly, device 10 is provided with flexion—of variable levels via neck 18 and collar 28—which allow the device to be particularly suited for cleaning hard to reach places.

Figure 5:
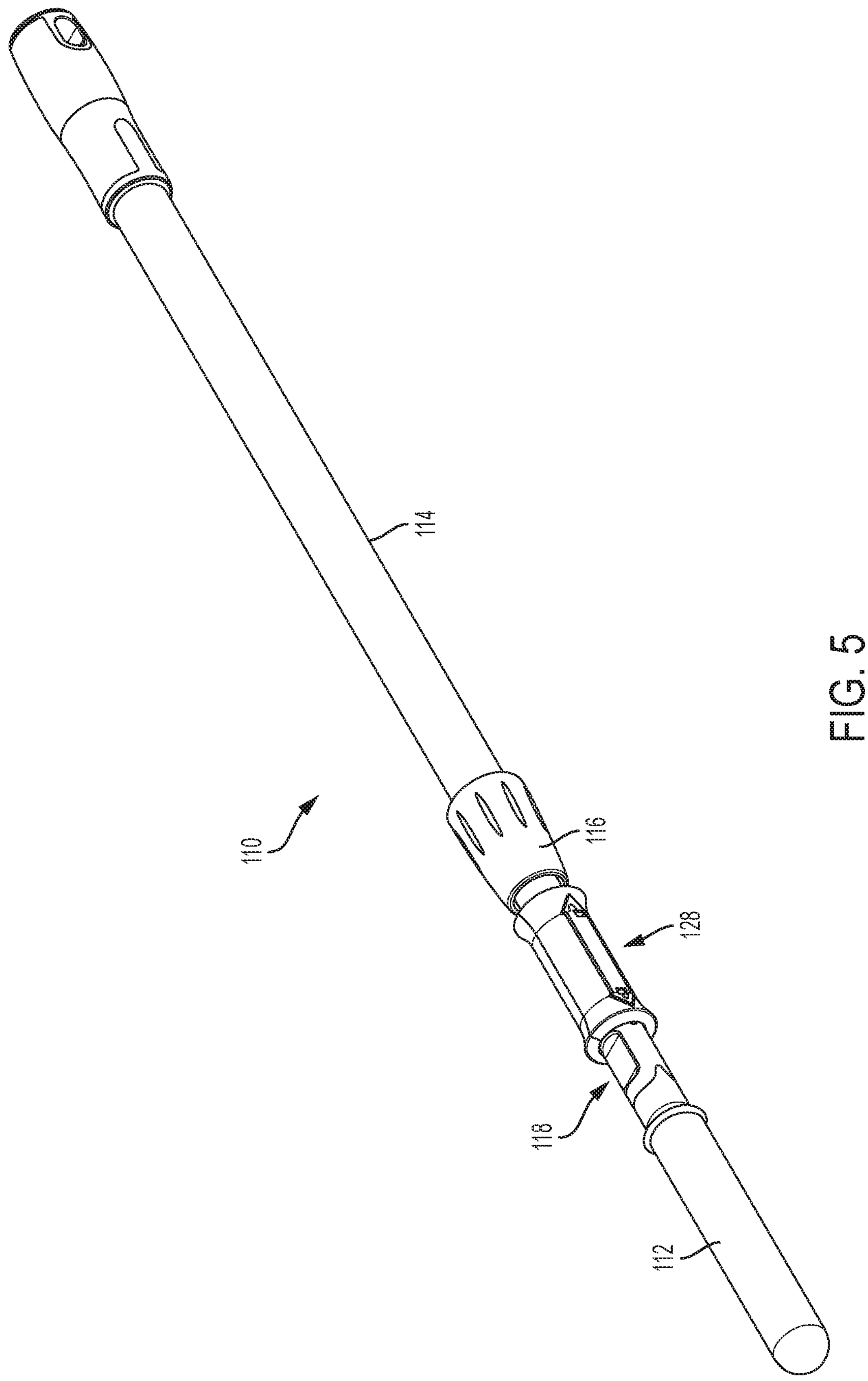
FIG. 5 is a perspective view an alternate exemplary embodiment of the cleaning device of FIG. 1 according to the present disclosure.

Referring now FIG. 5, an alternate embodiment of cleaning device according to the present disclosure is shown and is referred to by reference numeral 110. Here, component parts performing similar or analogous functions are labeled in multiples of one hundred with respect to cleaning device 10.

Cleaning device 110 is shown by way of example as having a cleaning implement 112 illustrated as a brush with the bristles removed for simplicity, but of course it is contemplated by the present disclosure for device 110 to find use with other cleaning implements. Device 110 can include one or more features such as, but not limited to, a handle or handle 114 and a telescoping device 116, which allows the handle to be telescope between extended and retracted positions in a known manner.

Device 110 includes a flexible neck 118. In some embodiments, neck 118 provides a first level of flexion in a first orientation, but a second, lower level of flexion in a second orientation. In other embodiments, neck 118 provides equal levels of flexion in all orientations. Advantageously, device 110 has a flexion collar 128 that slides with respect to neck 118 between a first position where movement of the neck is unrestricted by the collar and a second position where movement of the neck is restricted by the collar.

Figure 6:
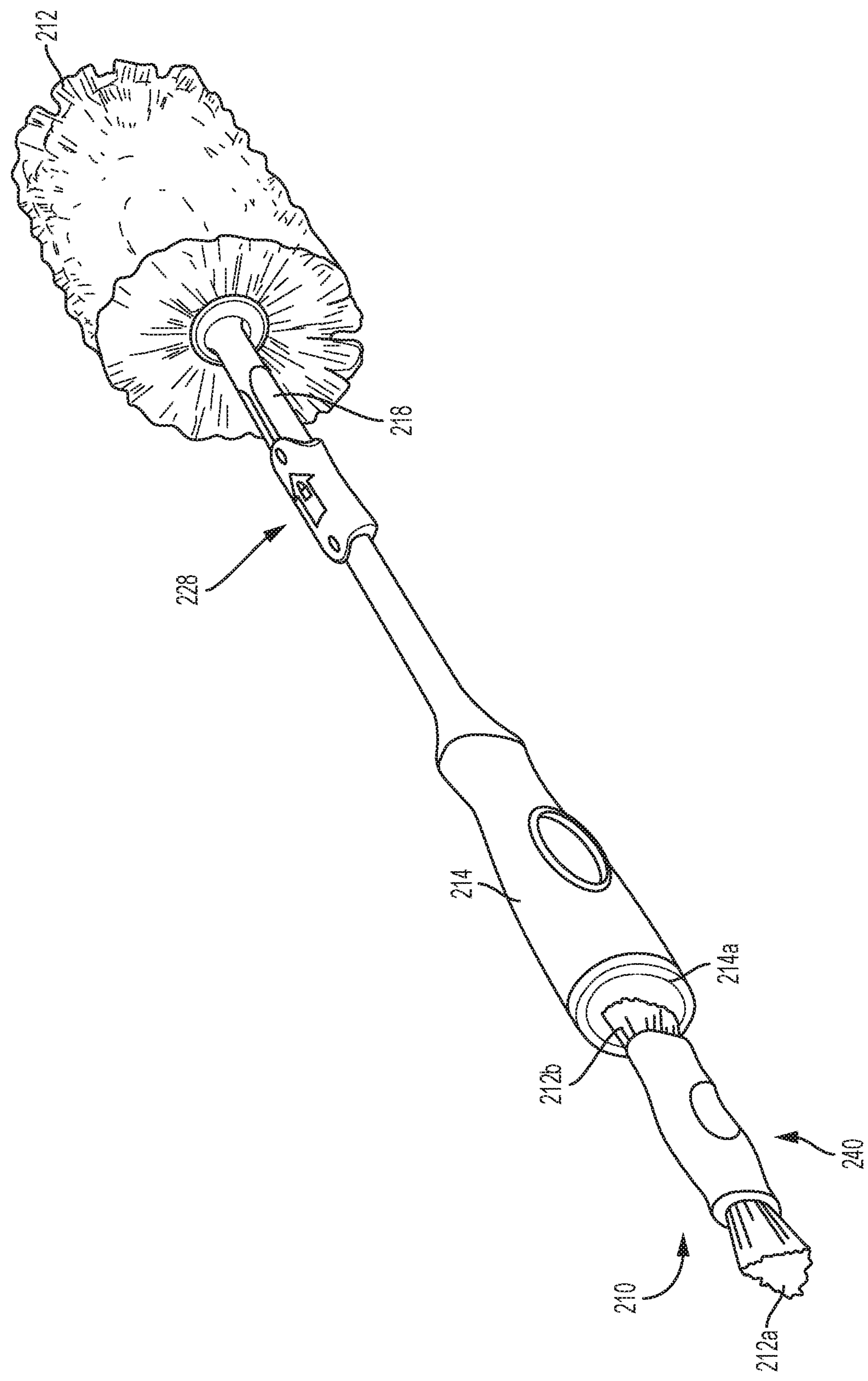
FIG. 6 is perspective, exploded view of another alternate embodiment of a cleaning device according to the present disclosure.
Figure 7A:
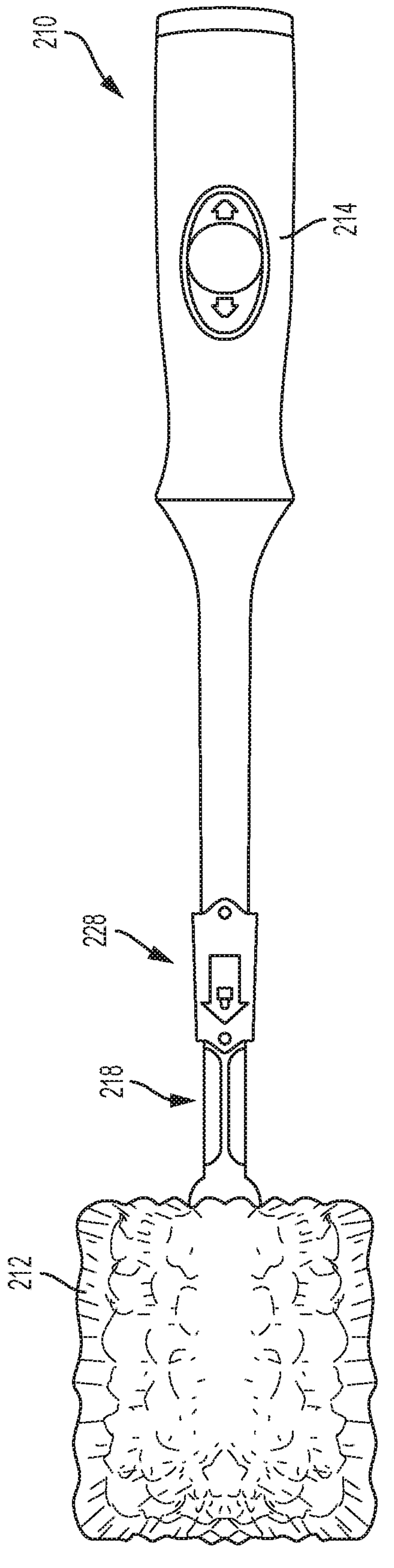
FIG. 7A is a top view of the cleaning device of FIG. 6 in an assembled state.
Figure 7B:
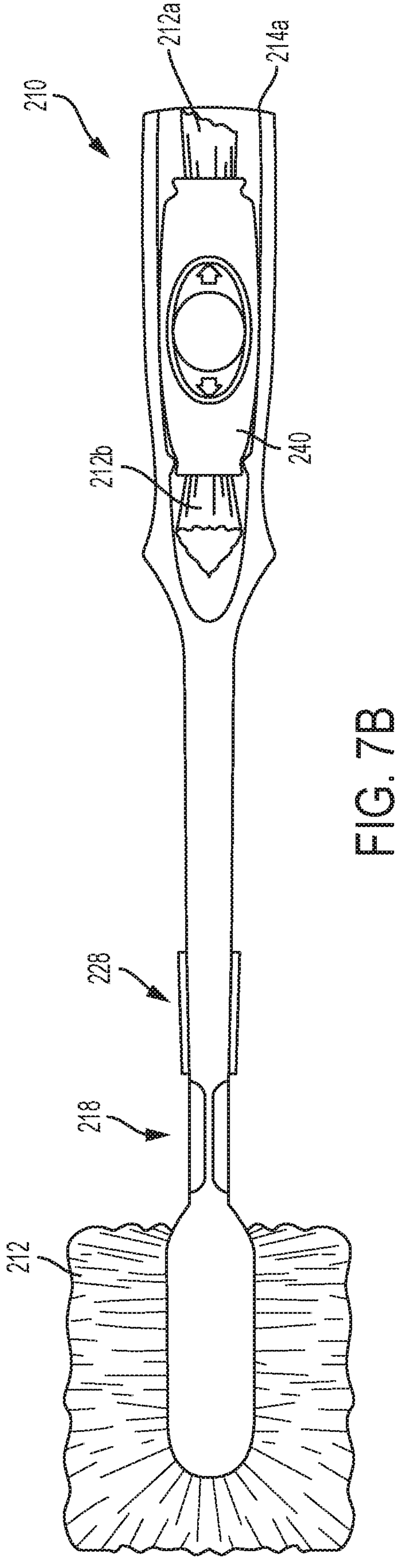
FIG. 7B is a partial sectional view of the cleaning device of FIG. 7A.
Figure 8:
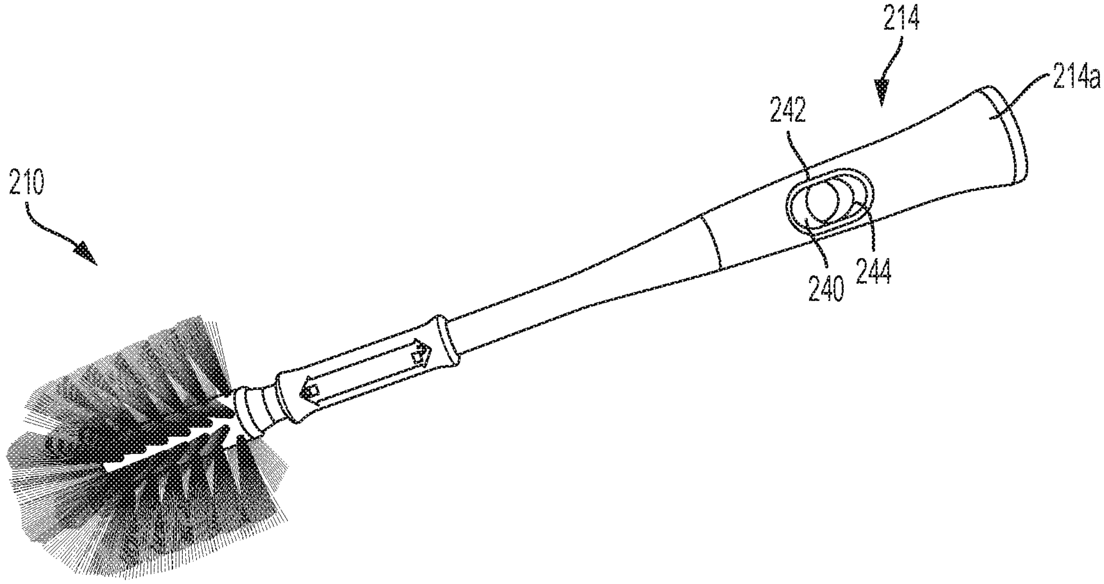
FIGS. 8 through 12 illustrate an exemplary embodiment of a detail brush removal method from the cleaning device of FIG. 6.
Figure 9:
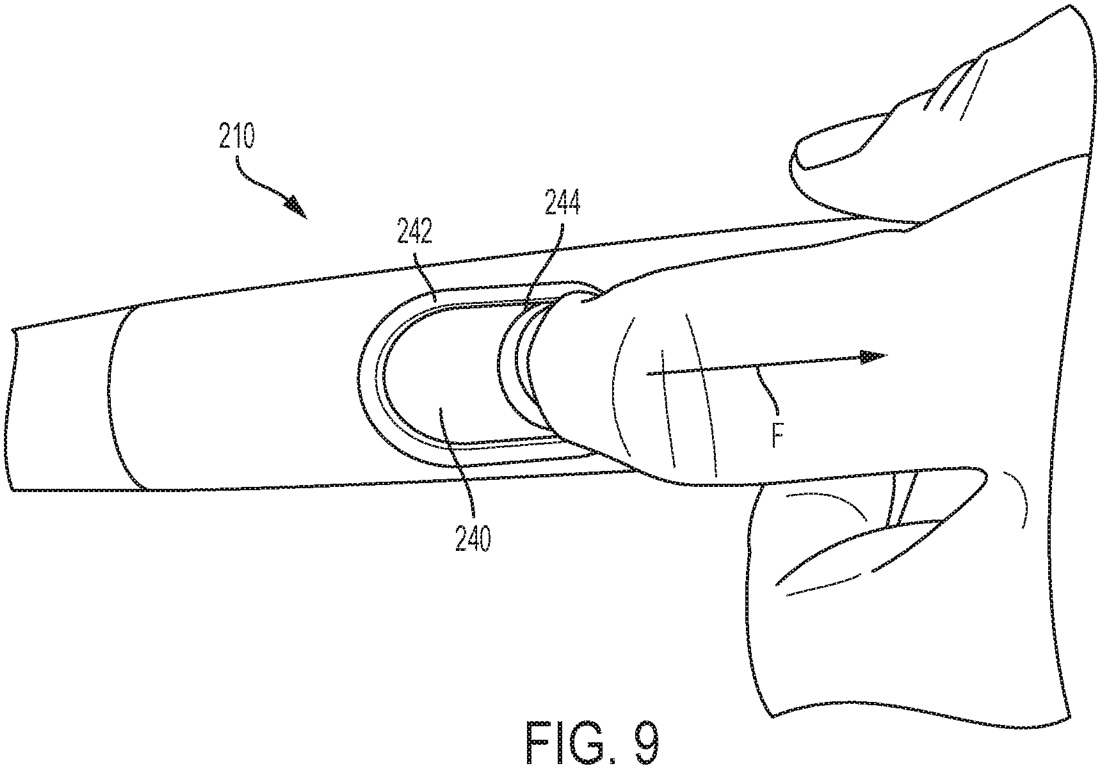
Figure 10:
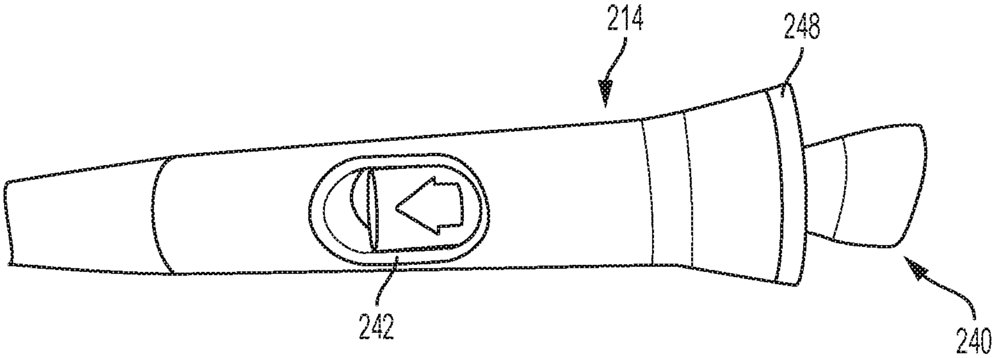
Figure 11:
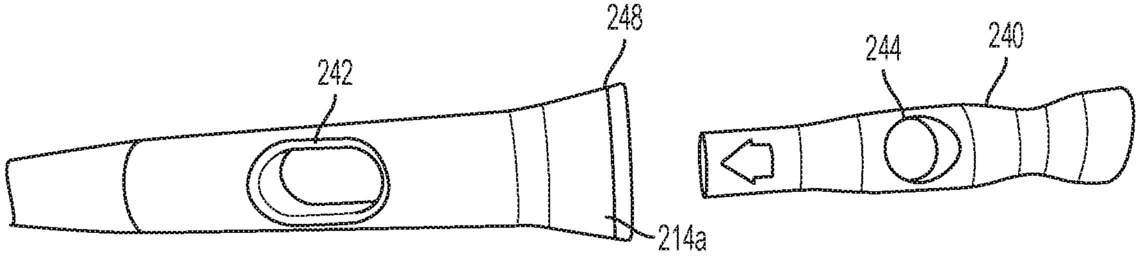
Figure 12:
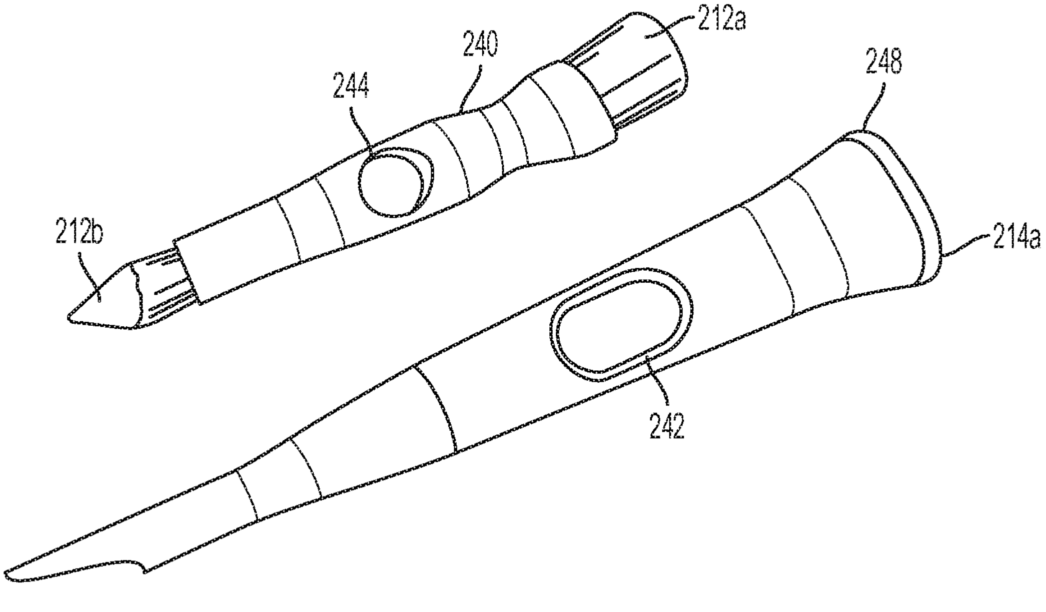

Referring now to FIGS. 6, 7A, and 7B, another alternate exemplary embodiment of cleaning device is shown and is referred to by reference numeral 210. Here, component parts performing similar or analogous functions are labeled in multiples of two hundred with respect to cleaning device 10.

Device 210 includes a cleaning implement 212 and a handle or pole 214 (hereinafter "handle"). Device 210 is shown by way of example as having a cleaning implement 212 illustrated as a brush, but of course it is contemplated by the present disclosure for device 210 to find use with other cleaning implements.

Device 210 can, in some embodiments, include a neck 218 alone or in combination with a collar 228. Neck 218 and collar 228, when present, can be as disclosed elsewhere herein.

Device 210 can include a nested detail cleaning device 240 disposed within a free end 214*a* of handle 214 opposite cleaning implement 212. Detail device 240 includes additional cleaning implements 212*a*, 212*b*—illustrated as brushes—on one or more ends (both illustrated). In this manner, the user can clean larger surfaces with cleaning implement 212, and can clean smaller or more detailed areas with cleaning implements 212*a*, 212*b* of device 240.

It should be recognized that nested device 240 is shown by way of example only as having brush bristles as cleaning implements 212*a*, 212*b*. Of course, it is contemplated by the present disclosure for nested device 240 to have one or more of any desired cleaning implement(s) 212*a*, 212*b* that are the same as or different from implement 212 and/or for detail device 240 to include any desired cleaning implements 212*a*, 212*b* on one or both ends. For example, it is contemplated by the present disclosure for detail device 240 to include cleaning implements 212*a*, 212*b* such as, but not limited to, a duster, a scrubber, a scraper, a squeegee, a mop, and any combinations thereof.

Advantageously, device 210 is configured so that detail device 240 is—even when having cleaning implements 212*a*, 212*b* on both ends—is entirely within handle 214. Thus and as used herein, the term "nested" shall mean that detail device 240—including cleaning implements 212*a*, 212*b*—does not extend, along the longitudinal axis, beyond free end 214*a* of handle 214.

To allow for removal of detail device 240 from device 210, device 210 includes a first opening 242 in handle 214 that allows access to nested device 240. Moreover, nested device 240 can include a second opening 244. In the assembled position, first and second openings 242, 244 are in registration with one another. In this manner and as shown in FIGS. 8-12, the user can place a finger through openings 242, 244 to apply a downward force (F) onto nested device 240 to force the nested device from handle 214. Similarly, the user can place a finger through holes 242, 244 to apply an upward force onto nested device 240 to force the nested device into handle 214 during assembly. Here, it can be seen that opening 242 is elongated to allow movement of the user's finger during installation and removal of the nested device 240. In this embodiment, the term nested also means that detail device 240 does not extend outward beyond handle 214.

Figure 13A:
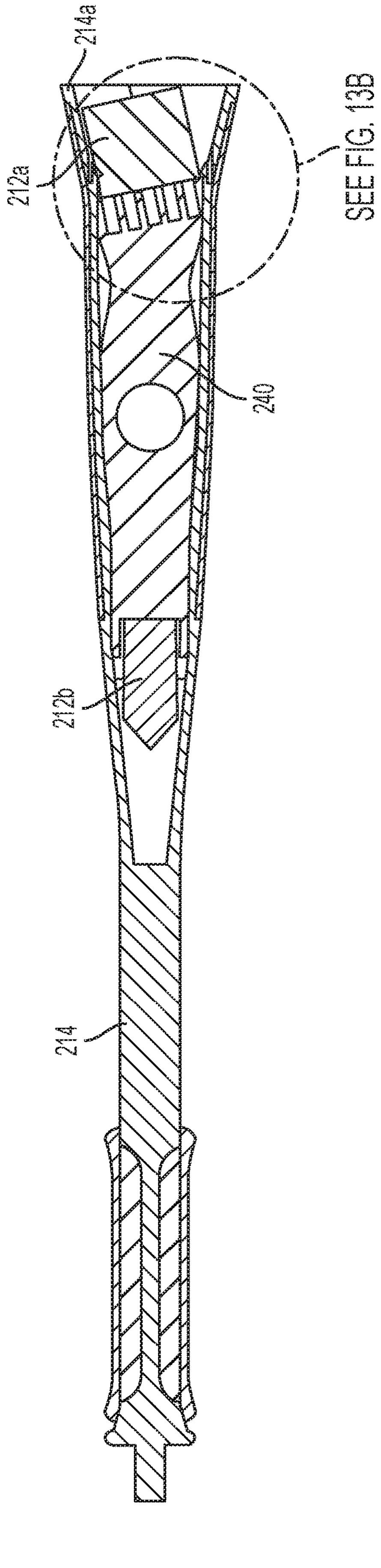
FIG. 13A is a sectional view of the cleaning device of FIG. 6.
Figure 13B:
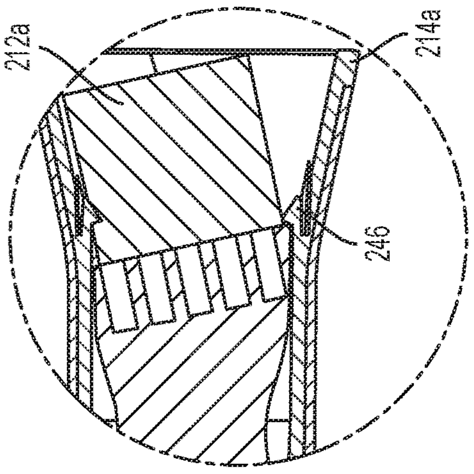
FIG. 13B is a partial magnified view of the cleaning device of FIG. 13A.
Figure 14:
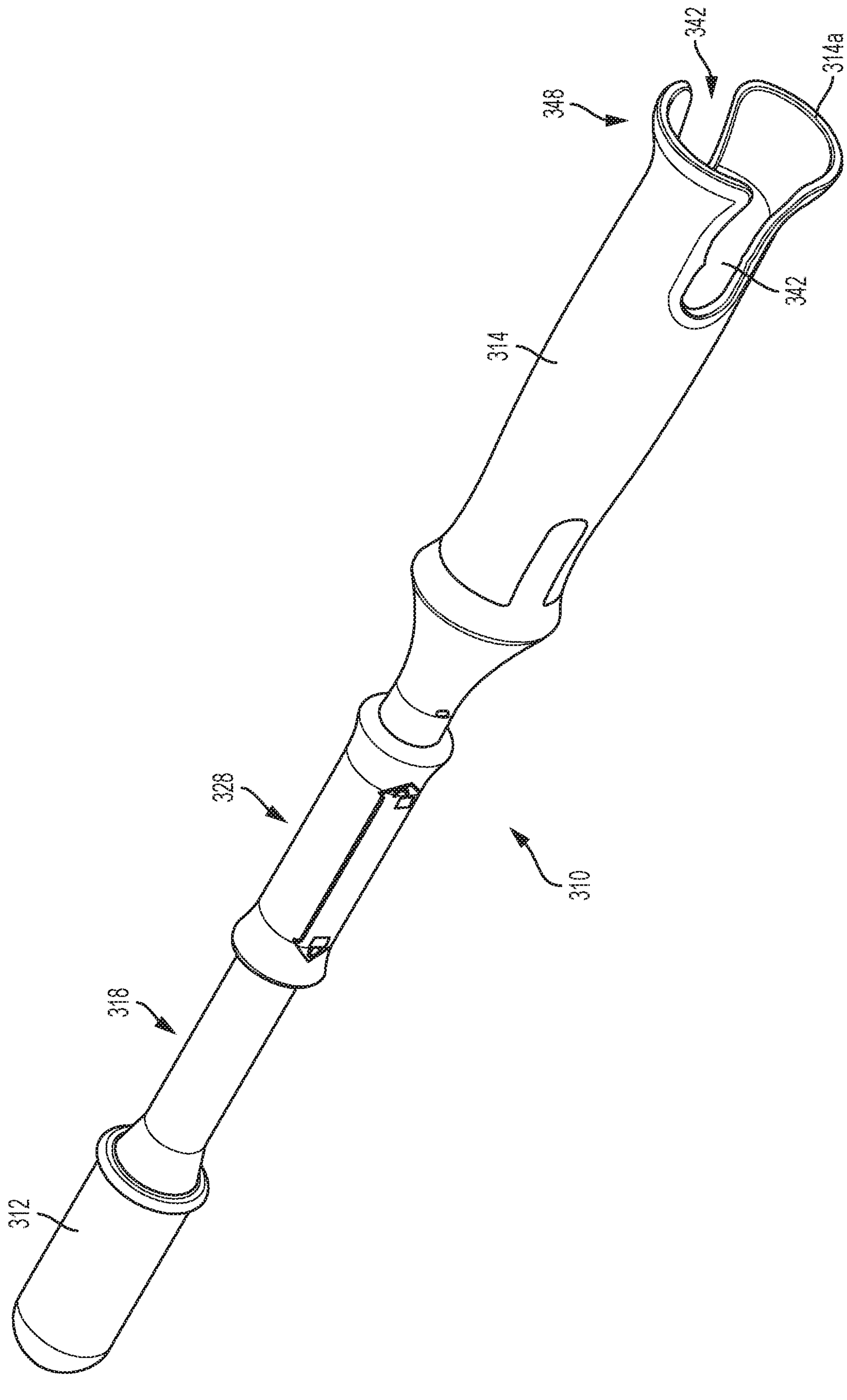
FIG. 14 is a perspective view an alternate exemplary embodiment of the cleaning device of FIG. 6 according to the present disclosure.
Figure 15B:
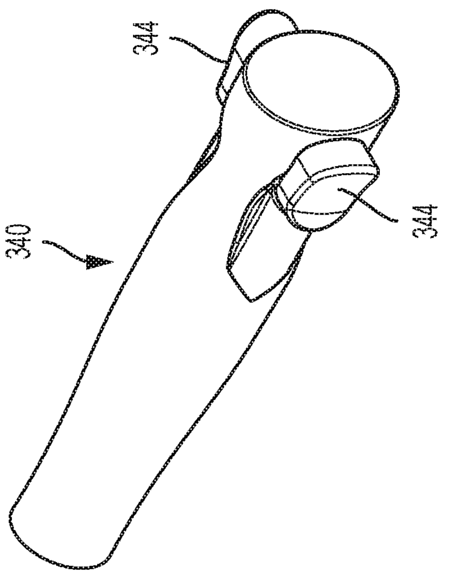
FIGS. 15A and 15B are perspective views of an exemplary embodiment of a detail brush for use with the cleaning device of FIG. 14.
Figure 15A:
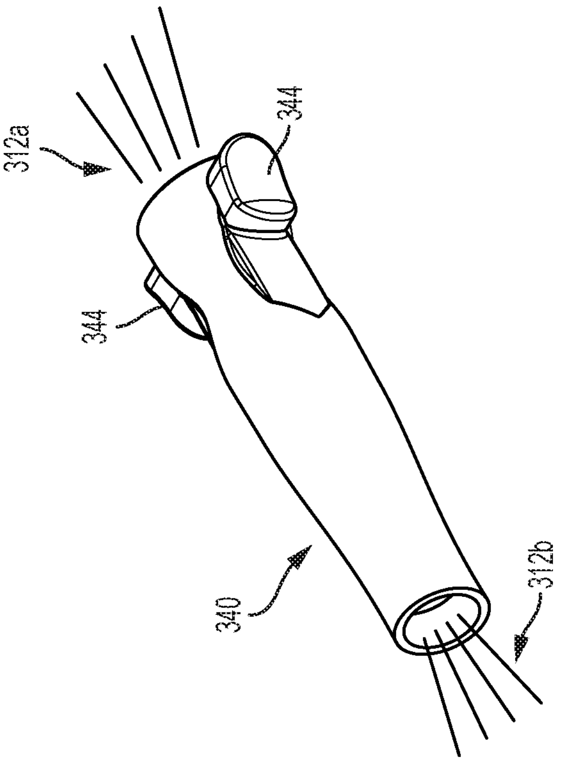

Nested device 240 can be selectively held in handle 214 in any desired manner such as, but not limited to the locking features 246 illustrated in FIGS. 13A and 13B. Features 246 can be on handle 214, device 240, or both the handle and the device.

Device 210 can include flared end 248 at open end 214*a*. It has been found by the present disclosure that, when nested device 240 includes brush bristles, flared end 248 can minimize damage to the nested device (i.e., brush bristles) during installation into handle 214.

Accordingly, device 210 provides the user with the ability to clean with cleaning implement 212—as well as implements 212*a*, 212*b* of detail device 240—which allow the device to be particularly suited for cleaning hard to reach places and allow the detail device to be readily available for specific cleaning functions such as, but not limited to, a detailed cleaning process.

Referring now FIGS. 14 through 17, an alternate embodiment of cleaning device according to the present disclosure is shown and is referred to by reference numeral 310. Here, component parts performing similar or analogous functions are labeled in multiples of three hundred with respect to cleaning device 10.

Cleaning device 310 is shown by way of example as having a cleaning implement 312 illustrated as a brush with the bristles removed for simplicity, but of course it is contemplated by the present disclosure for device 310 to find use with other cleaning implements. Device 310 can include one or more features such as, but not limited to, a handle or handle 314, neck 318, and collar 328.

Device 310 includes a nested detail cleaning device 340 disposed within free end 314*a* of handle 314. Detail device 340 includes additional cleaning implements 312*a*, 312*b*—illustrated in FIG. 14 as a brush with bristles which have been removed from FIGS. 15-17 for simplicity—on one or more ends (both shown).

Figure 16:
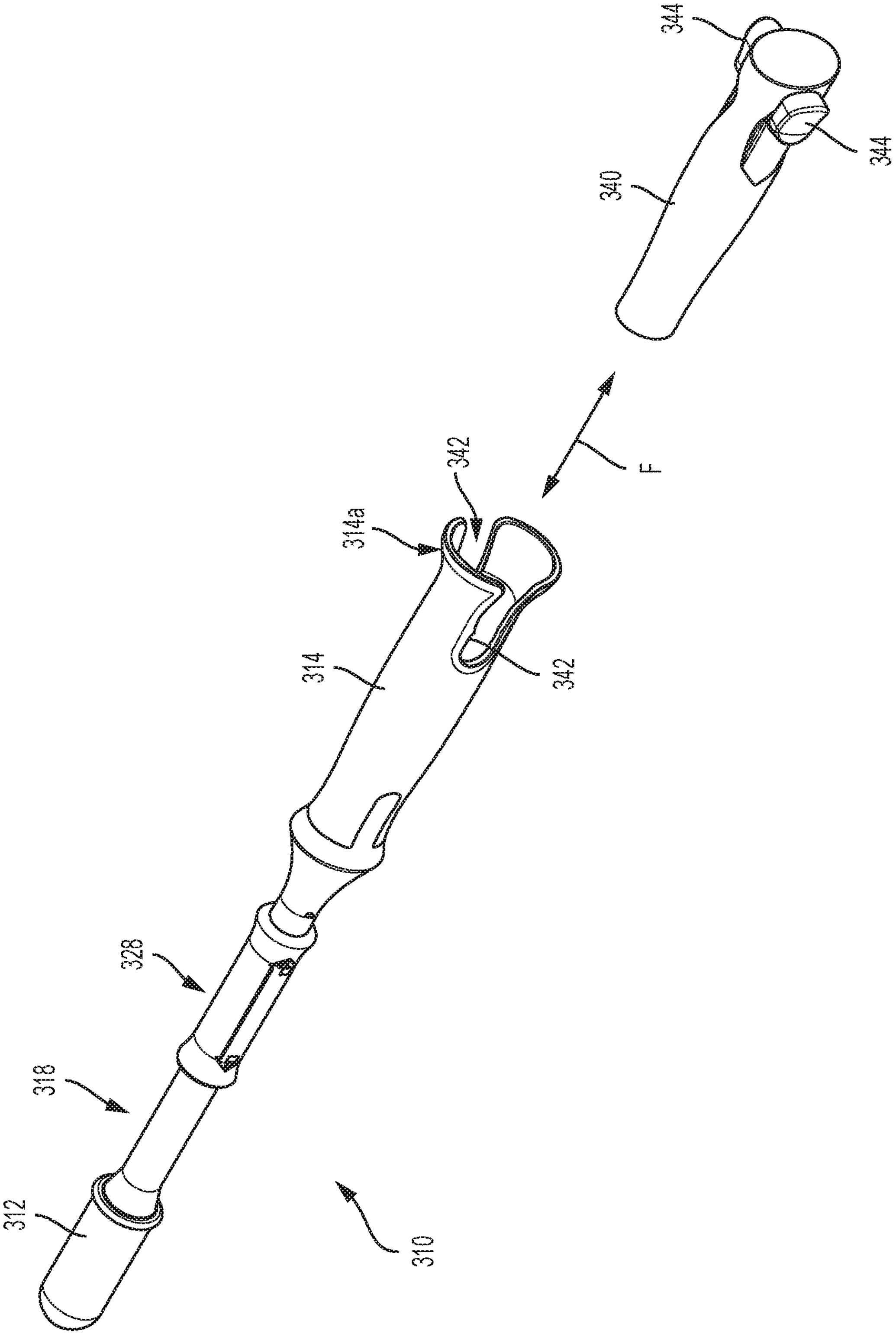
FIG. 16 is a perspective view of the assembly of the cleaning device of FIG. 14 and the detail brush of FIGS. 15A-15B.
Figure 17:
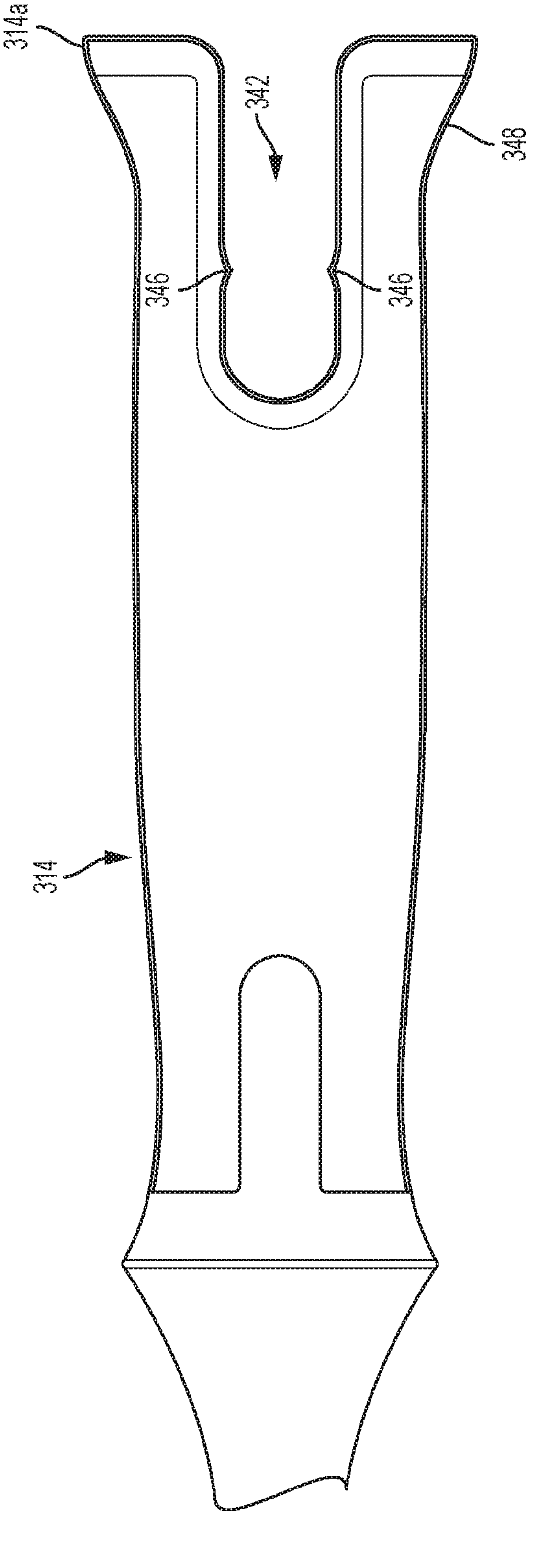
FIG. 17 is a partially magnified view of an end portion of the cleaning device of FIG. 6.

Device 310 includes a pair of elongated openings 342 in handle 314. Moreover, nested device 340 includes a corresponding pair of protrusions 344. In the assembled position, openings 342 receive protrusions 344 therein. In this manner and as shown in FIG. 16, the user can apply a force (F) to insert or remove nested device 340 from handle 314 in a longitudinal direction of the handle.

Nested device 340 can be selectively held in handle 314 in any desired manner. In the illustrated embodiment best shown in FIG. 17, openings 342 include one or more locking features 346 (two shown) disposed in at least one, but preferably both openings 342. Features 346 cooperate with protrusions 344 on device 340 to selectively secure the device in the handle 314.

During insertion and removal, protrusions 344 act on features 346 to deflect one or more regions of handle 314 that are proximate to openings 342 outward so that the protrusions 344 can pass over the features. It has been determined that the simple shape of elongated openings 342 allow the end region of handle 314 to deflect outward to provide a simple and repeatable locking feature to hold nested device 340 in handle 314, yet allow removal of the nested device when desired.

Again, device 310 is configured so that detail device 340 is—even when having cleaning implements 312*a*, 312*b* on both ends—is entirely within handle 314. Thus and as used herein, the term "nested" shall mean that detail device 340—including cleaning implements 312*a*, 312*b*-does not extend, along the longitudinal axis, beyond free end 314*a* of handle 314.

Device 310 can include flared end 348 at free end 314*a*. It has been found by the present disclosure that, when nested device 340 includes brush bristles, flared end 348 can minimize damage to the nested device (i.e., brush bristles) during installation into handle 314.

It should be recognized that nested device 340 is shown by way of example only as having brush bristles as cleaning implements 312*a*, 312*b*. Of course, it is contemplated by the present disclosure for nested device 340 to have one or more of any desired cleaning implement(s) 312*a*, 312*b* that are the same as or different from implement 312.

Accordingly, device 310 is provides the user with the ability to clean with cleaning implement 312—as well as via cleaning implement(s) 312*a*, 312*b* of detail device 340—which allow the device to be particularly suited for cleaning hard to reach places.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A cleaning device, comprising:
a handle;
a cleaning implement depending from one end the handle;
a flexible neck positioned to allow flexion of the handle in both a first orientation and a second orientation relative to a longitudinal axis of the handle, the second orientation rotated relative to the first orientation, wherein the flexible neck provides a first level of flexion in the first orientation and a second level of flexion in a second orientation the first level of flexion being different than the second level of flexion, wherein the flexible neck is a single unitary member comprising an upper region, a lower region, and a rib that are formed together with an elastomeric member over at least portions of the rib; and
a collar movable with respect to the flexible neck between a first position where movement of the flexible neck is unrestricted by the collar and a second position where movement of the flexible neck is restricted by the collar, wherein the collar has a first locking feature and the handle has a second locking feature complementary to the first locking feature, and the first locking feature cooperates with the second locking feature to selectively retain the collar in one of the first position and the second position.

2. The cleaning device of claim 1, wherein the collar moves with respect to the flexible neck in a manner selected from one of sliding along a longitudinal axis, rotating around the longitudinal axis, rotating about an axis perpendicular to the longitudinal axis, or radial clamping onto the longitudinal axis.

3. The cleaning device of claim 1, further comprising a telescoping device that allows the handle to telescope between extended and retracted positions.

4. The cleaning device of claim 1, wherein the elastomeric member encases the rib.

5. The cleaning device of claim 1, wherein the elastomeric member is over molded onto the rib.

6. The cleaning device of claim 1, wherein the elastomeric member provides elastomeric or resilient properties to the flexible neck.

7. The cleaning device of claim 1, wherein the elastomeric member has different elastomeric properties on one side of the rib as compared to an opposite side of the rib.

8. The cleaning device of claim 1, further comprising a nested detail cleaning device disposed within a free end of the handle opposite the cleaning implement.

9. The cleaning device of claim 1, wherein the neck has a stiffness ratio of flexion when the collar is in the first position to when the collar is in the second position of at least 1:2.

10. A cleaning device, comprising:
a handle;
a cleaning implement depending from one end the handle;
a flexible neck positioned to allow flexion of the handle, wherein the flexible neck is a single unitary member comprising an upper region, a lower region, a rib that connects the upper region and the lower region and an elastomeric member overlapping at least a portion of the rib, wherein at least one property of the elastomeric member varies about a periphery of the rib; and
a collar movable with respect to the flexible neck between a first position and a second position wherein in the first position, movement of the flexible neck is unrestricted by the collar and in the second position, movement of the flexible neck is restricted by the collar, wherein the collar has a first locking feature and the handle has a second locking feature complementary to the first locking feature, and the first locking feature cooperates with the second locking feature to selectively retain the collar in one of the first position and the second position.

11. The cleaning device of claim 10, wherein the collar moves with respect to the flexible neck in a manner selected from sliding along a longitudinal axis, rotating around the longitudinal axis, rotating about an axis perpendicular to the longitudinal axis, or radial clamping onto the longitudinal axis.

12. The cleaning device of claim 10, further comprising a telescoping device that allows the handle to telescope between extended and retracted positions.

13. The cleaning device of claim 10, further comprising a nested detail cleaning device disposed within a free end of the handle opposite the cleaning implement.

14. The cleaning device of claim 10, wherein the neck has a stiffness ratio of flexion when the collar is in the first position to when the collar is in the second position of at least 1:2.

* * * * *